United States Patent [19]
Blubaugh, Jr. et al.

[11] Patent Number: 5,964,993
[45] Date of Patent: *Oct. 12, 1999

[54] GLUCOSE SENSOR

[75] Inventors: Elmo A. Blubaugh, Jr., Springboro; Alan R. Brunsman, Yellow Springs, both of Ohio

[73] Assignee: Implanted Biosystems Inc., Kettering, Ohio

[*] Notice: This patent is subject to a terminal disclaimer.

[21] Appl. No.: 08/769,863

[22] Filed: Dec. 19, 1996

[51] Int. Cl.$^6$ .............................. G01N 27/26; C12N 11/02
[52] U.S. Cl. .......................... 204/403; 435/817; 435/180
[58] Field of Search .................................. 435/817, 180, 435/287.9; 204/403; 205/778, 792, 793, 777.5; 604/20

[56] References Cited

U.S. PATENT DOCUMENTS

| | | | |
|---|---|---|---|
| 4,146,438 | 3/1979 | de Nora et al. | 204/43 |
| 4,401,122 | 8/1983 | Clark, Jr. | 600/358 |
| 4,458,686 | 7/1984 | Clark, Jr. | 600/358 |
| 4,484,987 | 11/1984 | Gough | 205/778 |

(List continued on next page.)

OTHER PUBLICATIONS

Higson et al. ("Glucose oxidase enzyme electrode: relation between inner membrane permeability and substrate response", Analytica Chimica Acta, 276 (1993) 335–340).

Mullen et al. ("Glucose Enzyme Electrode with Extended Linearity", Analytica Chimica Acta, 183 (1986) 59–66).

An Idea Whose Time Has Come, by Shauna S. Roberts, *Diabetes Forecast*, May 1993, pp. 25–27.

Calcium phosphate naturally formed on titanium in electrolyte solution, by Takao Hanawa and Mamoru Ota, *Biomaterials*, 1991, vol. 12, Oct., pp. 767–774.

Potential Applications of Certain Nickel–Titanium (Nitinol) Alloys, by Simon Civjan, Eugene F. Hugen, and Laszlo B. DeSimon, U.S. Army Institute of Dental Research, Walter Reed Army Medical Center, Washington, DC 20212, U.S.A., *J Dent Res*, Jan.–Feb. 1975, vol. 54, No. 1, pp. 89–96.

Comparative Cell Culture Effects of Shape Memory Metal (Nitinol®), Nickel and Titanium: A Biocompatibility Estimation, by J.L.M. Putters, D.M.K.S. Kaulesar Sukul, G.R. DeZeeuw, A. Bijma, P.A. Besselink, *Eur. Surg. Res.*, 1992, pp. 378–382.

Elecrochemial and XPS studies of Titanium for biomaterial applications with respect to the effects of hydrogen peroxide, by J. Pan, D. Thierry, and C. Leygraf, *Journal of Biomedical Materials Research*, vol. 28, 113–122 (1994), pp. 113–122.

*Primary Examiner*—William H. Beisner
*Assistant Examiner*—Alex Noguerola
*Attorney, Agent, or Firm*—Thompson Hine & Flory LLP

[57] ABSTRACT

A sensor that is capable of accurately measuring glucose and other analytes in low oxygen environments is provided. The sensor employs an enzyme-containing membrane comprising a semi-interpenetrating polymer network which is infiltrated by an enzyme. The enzyme-containing membrane increases oxygen transport to the enzyme such that oxygen is not a limiting factor in the oxidation taking place at the enzyme.

31 Claims, 3 Drawing Sheets

U.S. PATENT DOCUMENTS

| | | | |
|---|---|---|---|
| 4,680,268 | 7/1987 | Clark, Jr. | 205/778 |
| 4,703,756 | 11/1987 | Gough et al. | 600/347 |
| 4,721,677 | 1/1988 | Clark, Jr. | 204/403 |
| 4,757,022 | 7/1988 | Shults et al. | 204/403 |
| 4,759,828 | 7/1988 | Young et al. | 205/778 |
| 4,832,009 | 5/1989 | Dillon | 602/58 |
| 4,849,085 | 7/1989 | Debrodt et al. | 204/290 F |
| 4,849,205 | 7/1989 | Hong | 423/644 |
| 4,849,285 | 7/1989 | Dillon | 428/330 |
| 4,859,383 | 8/1989 | Dillon | 264/43 |
| 4,871,366 | 10/1989 | von Recum et al. | 623/11 |
| 4,931,213 | 6/1990 | Case | 252/507 |
| 4,938,850 | 7/1990 | Rothschild et al. | 205/191 |
| 4,941,201 | 7/1990 | Davis | 455/41 |
| 4,945,125 | 7/1990 | Dillon et al. | 524/427 |
| 4,983,474 | 1/1991 | Doi et al. | 429/59 |
| 4,994,167 | 2/1991 | Shultz et al. | 204/403 |
| 5,019,140 | 5/1991 | Bowser et al. | 96/6 |
| 5,030,333 | 7/1991 | Clark, Jr. | 205/777.5 |
| 5,066,683 | 11/1991 | Dillon et al. | 174/59 |
| 5,157,058 | 10/1992 | Dillon et al. | 521/134 |
| 5,205,921 | 4/1993 | Shirkanzadeh | 205/318 |
| 5,260,701 | 11/1993 | Guern et al. | 340/825.54 |
| 5,322,063 | 6/1994 | Allen et al. | 600/347 |
| 5,352,348 | 10/1994 | Young et al. | 205/778 |
| 5,354,390 | 10/1994 | Haszmann et al. | 48/518 |
| 5,362,553 | 11/1994 | Dillon et al. | 442/76 |
| 5,399,250 | 3/1995 | Moon et al. | 204/255 |
| 5,429,895 | 7/1995 | Lian et al. | 429/223 |
| 5,476,589 | 12/1995 | Bacino | 210/500.36 |
| 5,531,878 | 7/1996 | Vadgama et al. | 204/415 |

GLUCOSE SENSOR

BACKGROUND OF THE INVENTION

1. Field of the Invention

The present invention relates to glucose sensors and, more particularly, to a membrane that is useful in a glucose sensor as well as other applications employing enzymes in which efficient oxygen transport to the site of the enzyme would be desirable.

2. Description of Related Art

There is currently a considerable need for a glucose sensor that can accurately measure glucose levels in low oxygen environments, and more particularly, a sensor that can be readily implanted into a human where it will function for a prolonged time period. The primary impetus for such a device is the disease known commonly as diabetes. It has been known for well over fifty years that this disease is primarily a result of inadequate secretion of the hormone insulin by the islet or Beta cells of the pancreas. When uncontrolled, this disease often leads to serious metabolic imbalances as the elevated glucose level leads to ketosis and damaging alterations in blood pH. However, life threatening swings in blood glucose are now largely controlled by diet and daily injections of insulin.

For decades it has been realized that control of diabetes by insulin injection usually results in much wider swings in blood glucose level than are common in a normal individual. However, the conventional wisdom was that only extremes in blood glucose level need be avoided. Nevertheless, occasional insulin injections (i.e., one to several per day) are unable to duplicate the strict control of blood glucose afforded by a properly functioning pancreas which continually meters out just enough insulin to maintain stable and relatively low blood glucose levels.

Despite avoiding extremes in blood glucose level insulin-dependent diabetics suffer a whole host of other maladies that decrease both the quality and quantity of life. Diabetics experience frequent vascular disease that often result in amputation of limbs as impaired circulation prevents adequate blood flow. Abnormal vascular growth within the eye may result in intraocular bleeding, and retinal damage with progressive loss of vision. Nerve degeneration may lead to loss of sensation and other related problems. As home glucose tests became common, more and more data became available demonstrating the relatively poor control of blood glucose afforded by periodic insulin injections. At the same time, a growing number of clinical studies demonstrated that strict control of blood glucose reduces many if not all of the diabetes-related diseases previously mentioned. Many scientists and physicians now believe that greatly improved blood glucose control can largely eliminate the mortality and morbidity associated with diabetes.

Scientists are working on automatic insulin injection systems that deliver exogenously supplied insulin as needed to maintain precise blood glucose control. A self-regulating artificial insulin source is needed to limit the damage caused by diabetes. Many types of regulated injection systems, both implantable and external, are already available. The key problem continues to be the need for an accurate glucose sensor to control these injection systems. The need to continually monitor glucose levels to permit constant metered dispensing of insulin generally eliminates methods relying on blood samples. It is clear that an implantable glucose sensor that measures in vivo glucose levels is needed.

Although there are a number of technologies that could potentially be used to create an implantable glucose sensor, the most favorable method seems to be some type of amperometric method. The chemical reaction most commonly used in enzyme coupled glucose sensors is the glucose oxidase mediated catalytic oxidation of glucose by atmospheric oxygen to produce gluconolactone and hydrogen peroxide (equation 1):

$$C_6H_{12}O_6 + O_2 + H_2O \rightarrow C_6H_{12}O_7 + H_2O_2 \qquad (1)$$

In the presence of excess oxygen, the quantity of hydrogen peroxide produced in this reaction will be a direct measure of the glucose concentration. The hydrogen peroxide is detected by being reoxidized by an electrode (anode) maintained at a sufficient positive potential (equation 2):

$$H_2O_2 - 2e^- \rightarrow O_2 + 2H^+ \qquad (2)$$

The glucose detection process is dependent upon the measurement of electrons removed from hydrogen peroxide in equation (2). The electrode is normally formed from a noble metal such as gold or platinum, the usually preferred metal.

It is well known to those of ordinary skill in the art that other specific hydrogen peroxide producing oxidase enzymes can be used to produce sensors for other substances such as cholesterol (cholesterol oxidase), amino acids (amino acid oxidase), alcohol (alcohol oxidase), lactic acid (lactic acid oxidase), and galactose (galactose oxidase) to name only a few. While this approach operates effectively to measure glucose under laboratory conditions, there are major impediments to using this approach in an implantable glucose sensor. In particular, glucose is extremely soluble in biological fluids whereas oxygen is poorly soluble in these same fluids and must be carried by specialized biomolecules such as hemoglobin. As a result, many tissues of the human body have an oxygen concentration equivalent to about 2–5% oxygen in nitrogen or lower. There may be a ratio of glucose to oxygen as high as 100 to 1 in subcutaneous and peritoneal fluids. This means these tissues may contain only 1% of the oxygen required for glucose oxidase to quantitatively oxidize glucose for measurement purposes.

Furthermore, the glucose oxidase of a glucose sensor must be protected from processes and other macromolecules which might destroy or inhibit the glucose oxidase, from enzymes such as catalase which destroy hydrogen peroxide, from microbes which would digest the enzymes, and from soluble compounds such as ascorbate which would interfere with the either the enzymatic or electrochemical reactions. This protection is achieved by separating the glucose oxidase from biological fluids by a semipermeable membrane, The best known membranes that are capable of selectively excluding proteins such as catalase while allowing the entry of glucose are so-called dialysis membranes. These membranes are generally hydrophilic membranes containing pores that readily admit neutral molecules with molecular weights below about 5,000 Daltons. Common examples of these membranes are membranes prepared from various regenerated celluloses such a spectrapore or cuprophane, polycarbonate, cellulose esters, and polysulfones.

Unfortunately, while semipermeable membranes do a good job of excluding undesirable proteins, they also exclude oxygen. Some membranes such as those of teflon (perfluorocarbon resins) or of silicone rubber are permeable to oxygen, but these membranes are virtually impermeable to glucose, and hence, cannot be used to protect a glucose sensor. U.S. Pat. No. 5,322,063 to Allen et al. reports a new type of polyurethane membrane said to allow some glucose permeability while favoring oxygen permeability. This might represent one solution to the unfavorable glucose to oxygen ratio of human tissues; however, these membranes have not been widely tested as yet.

Because of a superabundance of glucose and a shortage of oxygen, an implanted glucose sensor will tend to be oxygen limited and, thus, effectively measure oxygen instead of glucose. That is, under ideal conditions where the glucose concentration is low, oxygen would be adequate so that an increase in glucose concentration would result in a concomitant and proportional increase in hydrogen peroxide and, therefore, measured current at the electrode. However, as the concentration of glucose increases, oxygen will ultimately become insufficient causing the measured current to plateau and become independent of glucose concentration. Above this plateau, the measured current reflects changes in oxygen concentration rather than glucose concentration.

Many workers have failed to take into account the high glucose to oxygen ratio of human tissues. There are at least two ways to solve this problem: one can attempt to reduce the concentration of glucose that reaches the glucose sensor and/or one can attempt to increase the amount of oxygen available at the glucose sensor. The level of glucose can be reduced either by providing a permeability barrier to glucose or by providing additional enzyme systems, besides glucose oxidase, to consume glucose. The polyurethane membrane mentioned above is an example of this approach.

Accordingly, there is a need for a glucose sensor, in particular, an implantable glucose sensor that can accurately measure glucose levels in low oxygen environments.

SUMMARY OF THE INVENTION

The present invention provides a membrane for use in a glucose or other enzyme-coupled sensor that enables the measurement of analyte levels in low oxygen environments, i.e., environments in which the oxygen concentration is less than stoichiometric. That membrane is an enzyme-containing membrane comprising a semi-interpenetrating polymer network of fibrillated polytetrafluoroethylene and a silicon compound wherein the network is infiltrated with an enzyme.

The glucose sensor of the present invention employs an outer membrane that is preferably tuned for maximum oxygen transport with minimum stirring effect and minimal reduction in glucose transport and an inner membrane, which is a novel enzyme-containing membrane, comprising a semi-interpenetrating network of fibrillated polytetraflouroethylene and a silicon compound which is infiltrated with an enzyme. This inner membrane enhances the transport of oxygen to the sites of glucose oxidation such that oxygen is not a limiting factor in the glucose oxidation reaction. In addition to being useful in the detection of glucose, it will be recognized that the membrane of the present invention can be used in any enzyme coupled analysis in which there is a need to enhance oxygen transport. The membrane may also be useful in certain enzyme reactors (bioreactors) in which enhanced oxygen transport would be desired.

Another manifestation of the invention is a method for determining glucose level within a subject comprising:

implanting a glucose sensor within a subject whose glucose level is to be monitored, wherein the glucose sensor includes a measuring electrode, a reference electrode, and a membrane system having an outer membrane and an inner membrane, wherein the inner membrane is disposed between the outer membrane and the measuring electrode and is an enzyme-containing membrane which includes a semi-interpenetrating polymer network of fibrillated polytetrafluoroethylene and a silicon compound, wherein the network is infiltrated by an enzyme, and wherein the outer membrane restricts the flow of glucose into the inner membrane; the measuring electrode being capable of oxidizing hydrogen peroxide; and measuring the current produced at the measuring electrode in oxidizing hydrogen peroxide and determining the glucose level.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a glucose sensor, and more particularly, an implantable glucose sensor based upon the detection of hydrogen peroxide and containing an enzyme-containing membrane comprising a semi-interpenetrating polymer network of fibrillated polytetrafluoroethylene and a silicon compound wherein the network is infiltrated with an enzyme.

Glucose sensors are used to measure glucose levels within a subject's body tissues. The glucose sensor of the present invention can be used externally or internally as an implantable sensor. Accurate measurements of glucose levels in very low oxygen environments are obtainable with the glucose sensor of the present invention. In order to achieve accurate measurements of glucose levels within the blood, the concentration of oxygen at the site of glucose oxidation must be greater than or equal to the glucose concentration at the site of glucose oxidation such that the glucose is the limiting factor in the oxidation reaction rather than the oxygen. To achieve and maintain this stoichiometric relationship at the site of glucose oxidation, the glucose concentration must be restricted and oxygen transport to the site of glucose oxidation must be enhanced.

Figure 1:
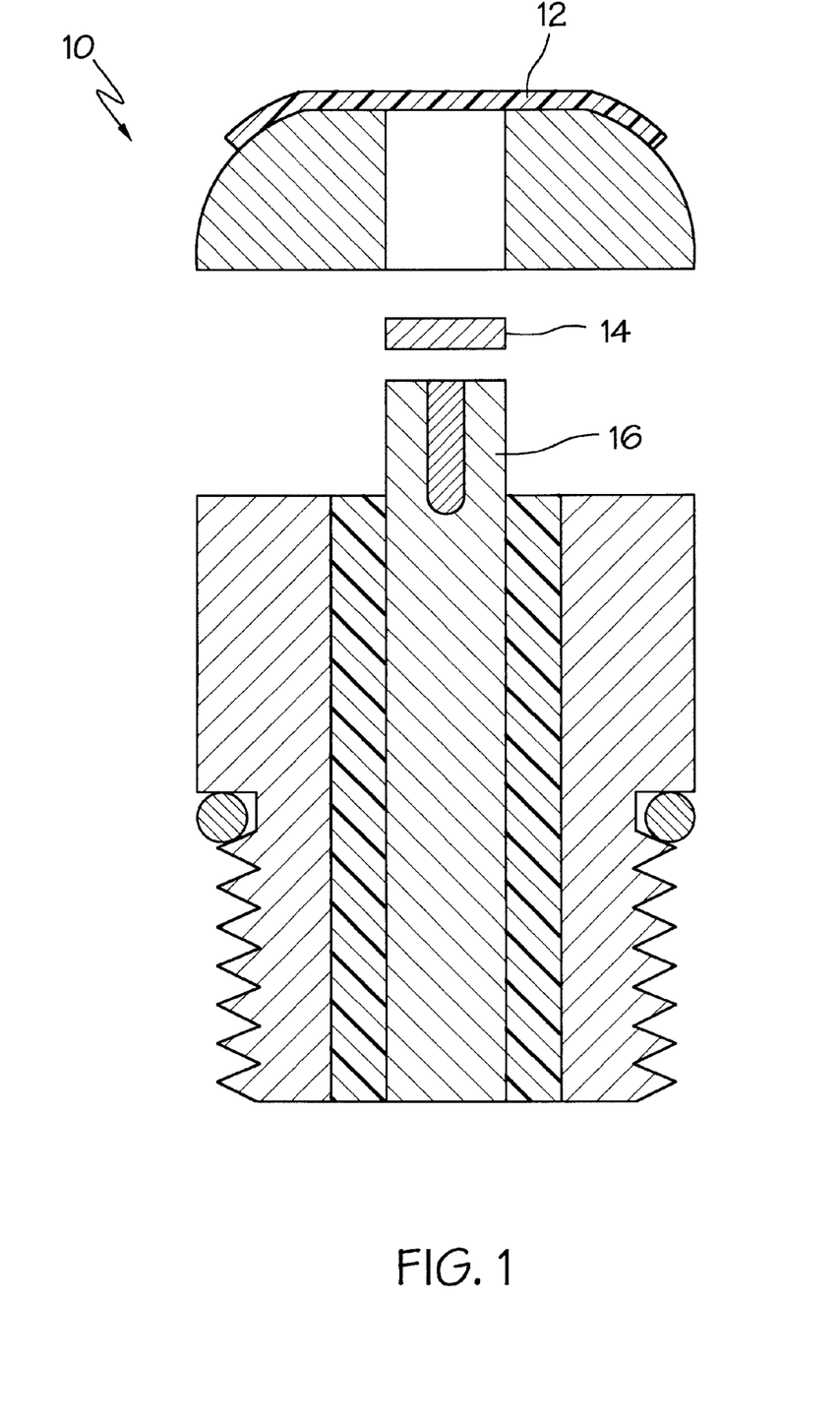
FIG. 1 is an exploded view of a schematic diagram of a glucose sensor in accordance with the present invention.

As shown in FIG. 1, a glucose sensor, in accordance with the present invention, generally designated 10, comprises a membrane system including an outer membrane 12 and an enzyme-containing membrane 14, and an electrode 16. The enzyme-containing membrane 14 is disposed between the outer membrane 12 and the electrode 16.

The electrode 16 can be any suitable electrode that is capable of detecting and measuring hydrogen peroxide. Preferably, the electrode 16 is a noble metal electrode, more preferably a platinum electrode. It is desirable that the surface of the electrode 16 is maintained electroactive to maximize the effectiveness of the glucose sensor. Furthermore, it is desirable that the electrode 16 does not change its sensitivity to hydrogen peroxide over time.

In operation, glucose and oxygen contained within the body tissues of a subject come into contact with the outer membrane 12 of the glucose sensor 10. The outer membrane 12 provides greater restriction to glucose than to oxygen and thus, reduces the concentration of glucose flowing through the outer membrane 12. The function of the outer membrane 12 is to affect the concentrations of glucose and oxygen such that after the glucose and oxygen have passed through the outer membrane 12, the concentration of oxygen is preferably greater than or equal to the concentration of glucose. By doing so, the outer membrane 12 establishes the stoichiometric relationship required for the glucose oxidation reaction.

After the stoichiometric relationship between the oxygen and the glucose has been established by the outer membrane 12, this stoichiometric relationship must be maintained at the sites of glucose oxidation, namely the enzymes contained within the enzyme-containing membrane 14. Maintaining this stoichiometric relationship at the enzymes is facilitated by the semi-interpenetrating polymer network and its enhancing effects on oxygen transport. Furthermore, the enzyme-containing membrane 14 creates a tortuous path for the glucose in its attempt to pass through the membrane, however, it does not restrict the flow of glucose to the enzymes. This added restrictive control on glucose and the enhanced oxygen transport to the enzymes, such that localized concentrations of oxygen are formed, ensures that the stoichiometric relationship is maintained at the enzymes. Therefore, at a particular enzyme, the concentration of oxygen at the enzyme is greater than or equal to the concentration of glucose at the enzyme. As a result of the stoichiometric relationship between oxygen and glucose at the enzymes, oxygen does not act as the limiting factor in the glucose oxidation reaction. Thus, the hydrogen peroxide generated during the glucose oxidation corresponds to the glucose present at the enzyme. Current flow representative of oxidation of hydrogen peroxide at the anode must be measured relative to a reference electrode so that a complete circuit is formed. The reference electrode is commonly provided by a silver or silver/silver chloride electrode in electrical contact with the body fluids.

The outer membrane 12 is preferably a polycarbonate but may consist of any other suitable solid porous or permeable material. The outer membrane reduces the rate of mass transport of the glucose through the membrane and yet does not interfere with the rate of mass transport of the oxygen through the membrane. Thus, the outer membrane 12 provides the restrictive control for the glucose. The outer membrane 12 also prevents catalase, an enzyme that destroys hydrogen peroxide, and other large molecules from passing through the membrane. The pore size and thickness of the outer membrane are selected to ensure that the passage of glucose through the outer membrane is sufficiently hindered in comparison to the passage of oxygen. In general, the thicker the membrane and the smaller the pore size, the more the passage of glucose will be hindered. In implantable glucose sensors, the outer membrane 12 must be made from a suitable biocompatible material.

One example of a membrane which is useful as the outer membrane 12 and which is commercially available is a polycarbonate membrane available from Poretics Corp. of Livermore, Calif. This membrane is available and employed in pore sizes of about 0.01 to 0.1 micron and pore densities of about $4 \times 10^8$ to $6 \times 10^8$.

The enzyme-containing membrane 14 comprises a semi-interpenetrating polymer network, made of fibrillated polytetrafluoroethylene (PTFE) and a silicon compound. This membrane is commercially available and a method for making this membrane is described in U.S. Pat. Nos. 4,945,125 and 4,832,009, and *Dillon, Silicone and Poly (tetrafluorolthylene) Interpenetrating Networks,* 1994, p. 393, which are incorporated herein by reference. The membrane can range in thickness from about 5 to $50\mu$. The membrane typically contains about 10 to 40% by volume of the silicon compound or elastomer. The porosity of the enzyme-containing membrane is from about 25% to about 55%.

The term "semi-interpenetrating polymer network" is used herein to refer to membranes prepared by the methods described in either of the aforementioned patents to Dillon and their functional equivalents. The method for making the semi-interpenetrating polymer network as described in U.S. Pat. No. 4,945,125 comprises the steps of: (1) intimately blending a mixture of a major amount of unsintered and unfibrillated particulate polytetrafluoroethylene dispersion resin (commercially available from E.E. du Pont de Nemours & Co., Inc., under the designations TEFLON® 6 and 6C and by Imperial Chemical Industries as FLUON® CD1, CD123 and CD525) and minor amounts of (A) a hydrocarbon liquid and (B) an addition curable silicone composition consisting essentially of a polydiorganosiloxane having alkenyl unsaturation, an organohydrogenpolysiloxane crosslinking agent, a catalyst for promoting crosslinking of the polysiloxane, and an inhibitor for the catalytic reaction; (2) forming the blend into an extrudable shape; (3) biaxially extruding the blend through a die into a shaped extrudate product having a randomly fibrillated structure; and (4) evaporating the hydrocarbon liquid, and activating the catalyst so as to generate a cured silicone elastomer and polytetrafluoroethylene semi-interpenetrating polymer network comprising the fibrillated extrudate structure.

Another method for making a semi-interpenetrating polymer network as described in U.S. Pat. No. 4,832,009 comprises the steps of: (1) blending polyorganosiloxane (commercially available from Dow Corning Corporation under the name SILASTIC® MDX4-4210) with a catalyst for promoting crosslinking of the polysiloxane in a 10:1 ratio; (2) mixing the blend with kerosene (commercially available from Fisher Scientific); and (3) applying the mixture to a substrate of expanded polytetrafluoroethylene film (commercially available from Tetratec Corporation of Feasterville, Penn.) by means of a spray apparatus.

Figure 2:
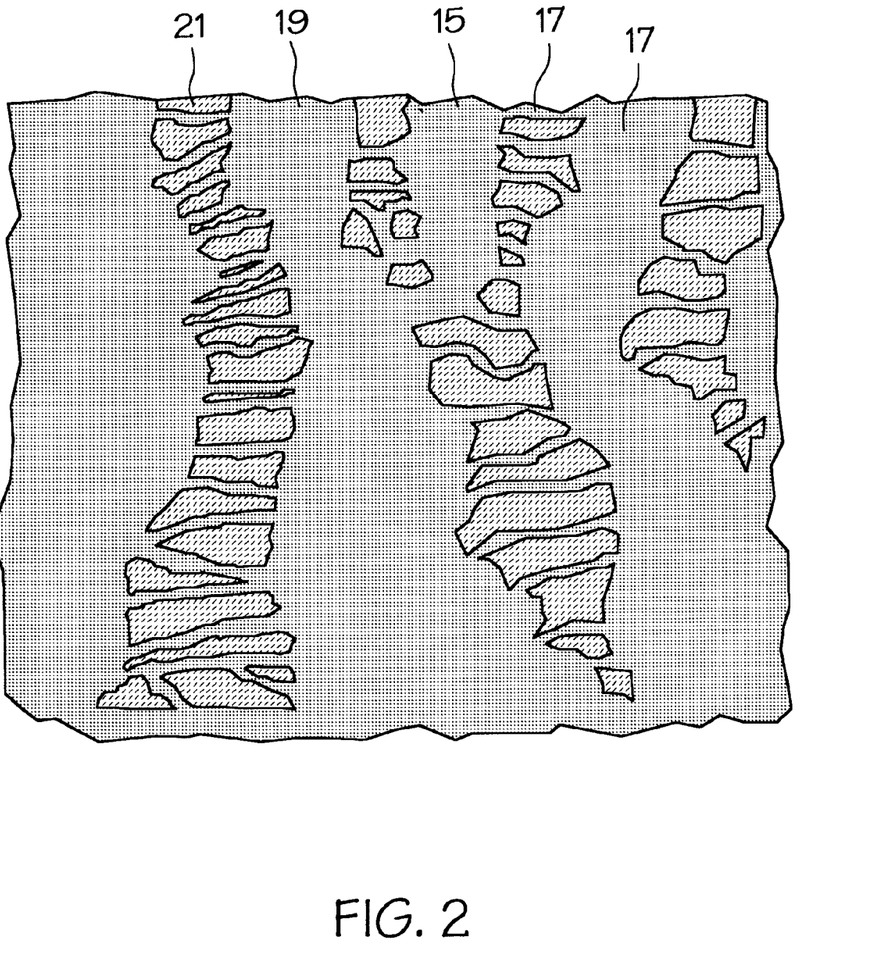
FIG. 2 is a schematic representation of a portion of an enzyme-containing membrane in accordance with the present invention.

Preferably, the silicon compound in the semi-interpenetrating polymer network is a cross-linked polyorganosiloxane, more preferably polydimethylsiloxane. The silicon compound facilitates the transport of oxygen to the sites of glucose oxidation. The semi-interpenetrating polymer network of fibrillated PTFE provides a porous membrane. The porosity of the membrane makes it possible to infiltrate it with the enzyme thus forming the enzyme-containing membrane 14, FIG. 1, a portion of which is represented by the schematic representation in FIG. 2. As shown in FIG. 2, the semi-interpenetrating network, generally designated 17, is a network of nodes 15 and fibrils 19 infiltrated with the enzyme 21. It has been found that by utilizing this semi-interpenetrating network, which has a very high affinity for oxygen, oxygen transport to the enzyme, the site of glucose oxidation, is increased resulting in an oxygen concentration that will be greater than or equal to the concentration of glucose at the enzyme. Less thick membranes improve the speed of detection or response. An example of a commercially available membrane that can be used in accordance with the invention is White Silon #320 from Biomed Sciences, Inc.

To facilitate the infiltration of the enzyme into the semi-interpenetrating network, it is desirable to treat the semi-interpenetrating polymer network with a surfactant. The surfactant renders the membrane hydrophilic. Preferably, the surfactant is a nonionic surfactant, more preferably, methyl terminated poly(dimethylsiloxane-b-ethylene oxide). However, it is anticipated that other surfactants can be used and especially surfactants with a silicon moiety and a hydrophilic moiety.

It is desirable that the enzyme is free from catalase activity, has a relatively long life, is very active and is a pure concentrate to maximize the effectiveness of the glucose sensor. Preferably, the enzyme is an oxidase, more preferably glucose oxidase (E.C. 1.1.3.4). Other useful enzymes have already been mentioned. It is also within the scope of the invention to use more complex systems employing a combination of enzymes. For example, enzyme systems are known in which a first enzyme reacts with an analyte to provide an intermediate which reacts with a second enzyme to produce the chemical species that is detected at the electrode.

The speed of oxygen diffusion through a barrier is controlled by the thickness of the barrier and by the amount of oxygen that can dissolve through a unit thickness of the barrier. That is, making the barrier thinner, i.e., bringing the analyte containing fluid closer, or making the barrier dissolve more oxygen will increase the rate of oxygen diffusion. Therefore, the enzyme-containing membrane 14 should be made as thin as feasible to maximize the rate of oxygen movement into the glucose sensor 10.

The enzyme can be immobilized within the interpenetrating network using a number of techniques. Preferably the enzyme is mixed with other proteins and crosslinked to form an enzyme gel as described below. However, other immobilization techniques may also be useful. For example, the silicon compound could be functionalized such that the enzyme could be covalently linked to the interpenetrating network. The enzyme can also be compounded with matrix formers, such as polymers, film-formeres or binders.

In one embodiment of the invention, the enzyme-containing membrane can be prepared by dissolving the enzyme in a solution of a carrier protein, such as an albumin, i.e., bovine serum albumin (BSA), and human albumin, or gelatin, in a suitable buffer such as 0.20 M sodium acetate buffer (pH=5.00). The enzyme concentration will vary depending upon the activity of the enzyme. Glucose oxidase is dissolved in the mixture at about 5 to 50% by weight. Amounts of alternative enzymes can be determined empirically based upon the activity of the particular enzyme. The enzyme mixture is applied to the semi-interpenetrating network and uniformly infiltrated into the semi-interpenetrating network by gently spreading the enzyme mixture on the membrane and rubbing with a smooth blunt spatula, thus resulting in an enzyme-containing membrane. Glutaraldehyde/acetate buffer is applied to the semi-interpenetrating network after the enzyme has been applied to crosslink the enzyme.

An alternative method may be used for infiltration of the enzyme into the semi-interpenetrating polymer network if the stabilized gel is to be based on a cross-linked protein gel. In this method, a suitable soluble carrier protein, such as an albumin, i.e., bovine serum albumin (BSA), and human albumin, or gelatin, at about 1 to 15% by weight final concentration is dissolved in a suitable buffer such as 0.2 M sodium acetate buffer, and an enzyme such as glucose oxidase is dissolved in the mixture at about 1% to 5% by weight final concentration. Sufficient purified glutaraldehyde as an aqueous 2.5% solution is added to dilute the protein solution to the correct final concentration. The final glutaraldehyde concentration following dilution is preferably between 0.1 and 1% and more preferably about 0.6%. This mixture is swirled briefly to mix and is then poured onto the membrane supported on glass plate and spread with a glass rod. Within a few hours a uniform layer of enzyme gel is formed. This gel is stored in a humidified atmosphere to prevent dehydration of the gel.

The incorporation of the novel enzyme-containing membrane into the glucose sensor of the present invention provides a glucose sensor that accurately measures glucose levels in extremely low oxygen environments such as 2% oxygen. In addition, the enzyme-containing membrane shows no decrease in response for at least about 2½ months. In fact, the enzyme-containing membrane's performance has been observed to improve as it ages.

The glucose sensor of the present invention comprises a measuring electrode, preferably a platinum anode, that is in contact with an aqueous fluid to be measured, e.g., the glucose-containing solution. A voltage source maintains the measuring electrode at a proper potential (here a positive potential to oxidize hydrogen peroxide). A reference electrode is also in contact with the glucose solution. The electrons removed from hydrogen peroxide at the measuring electrode flow through a conductor to the reference electrode where they complete the circuit by being returned to the aqueous solution. As the electrons pass through the conductor they are measured by an ammeter thus allowing the hydrogen peroxide to be quantitated.

It is apparent that all electrical contact with the solution must be made by means of the two electrodes. If there are other conductive pathways, current leakage would produce spurious current flows resulting in improper measurements. Where the electrodes simply dip into the aqueous solution, air insulates the remainder of the circuit and prevents current leaks. In implanted devices, the danger of current leaks becomes very great. As will be elaborated below, the present invention seals all of the electrical components in a small implantable package. In this case it is absolutely essential that the seal be water tight to avoid current leaks and to avoid water damage to the electronics.

An additional problem with implanted electrodes is that a significant current flow through the reference electrode often results in electrochemical side reactions that can damage a silver electrode and may also be toxic to the living tissue around the device. The solution to this problem seems to be the use of a third or auxiliary electrode. A third or auxiliary electrode, usually of a larger area and non-reactive material, takes the place of the reference electrode in returning the bulk of the current to the aqueous solution. The reference electrode is still in contact with the aqueous solution and a potentiostat senses the electrical potential of this electrode relative to the solution and fixes the auxiliary electrode at this potential so that the auxiliary electrode can act as a "surrogate" for the reference electrode. Because very little current flows through the reference electrode in this arrangement, there are no side reactions to damage the reference electrode or the surrounding living tissue.

A subject's glucose level can be determined by using the glucose sensor of the present invention by situating the glucose sensor within the subject and calculating the glucose level from the measuring electrode's response. For external use, the glucose level of a sample of blood from a subject can be determined by using the glucose sensor of the present invention and calculating the glucose level from the measuring electrode's response.

Figure 3:
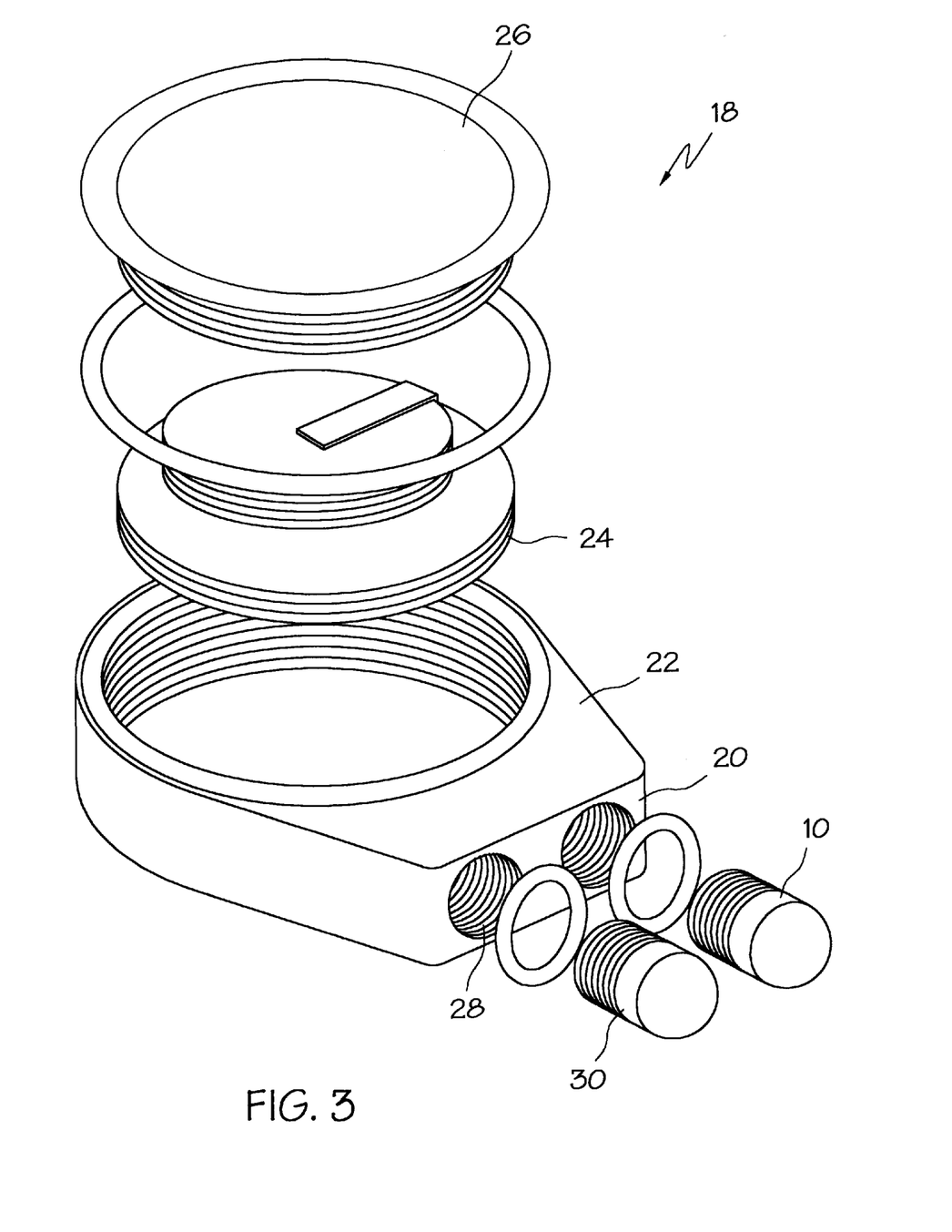
FIG. 3 is an exploded view of an implantable glucose sensor device employing the glucose sensor of the present invention.

As shown in FIG. 3, an implantable sensor device, generally designated 18, in accordance with the present invention may be disc shaped, although many other configurations are also possible. The device comprises an opening 20 and the glucose sensor 10, as shown in FIG. 1. Preferably, the device 18 is implanted beneath the surface of the skin with the opening 20 and glucose sensor 10 facing towards the underlying layer of muscle. This position allows ready access to the unit for repair or replacement. The device 18 can also be implanted so that the opening 20 and glucose sensor 10 face the peritoneal cavity. It is relatively important that the device 18 not be directly in contact with the circulatory system so that formation of blood clots does not interfere with the operation. It has been found that anticoagulants can be used to prevent clot formation. However, unless the patient requires anticoagulative therapy for some other reason, it is probably not prudent to require anticoagulation simply for an implantable glucose sensor device. All of the body tissues come into glucose equilibrium with the blood fairly rapidly so that placement of the device 18 in contact with the blood is not required.

The device 18 further comprises a housing, generally designated 22, which is shaped to receive the electronics for the device 18, for example a circuit board 24. The housing 22 includes a lid 26 which seals the electronics within the housing 22 via an O-ring. Furthermore, a second opening 28 is provided in the housing 22 to receive and fix a reference electrode, generally designated 30.

The device 18 also contains a miniature power supply, not shown, such as a lithium battery and microelectronics for transmitting a measured signal to a receiver outside of the human body. Transmission of data can be by means of radio waves, sound waves or even by means of modulated light. Although it is also possible to actually have a small wire connection to the device 18, this is not favored because of problems with infection at the point that the wire breaches the skin. Appropriate electronics are well known to those of skill in the art and will not be described further here.

A successful implantable sensor must make accurate measurements over a prolonged period of time and must be biologically compatible, i.e., not induce attempts by the body to reject the implants. Generally, biological compatibility is not an extremely serious problem for a housing of the sensor device. Implants made of a biocompatible material usually become surrounded by a layer of fibroblasts, but there are generally no episodes rejection. A number of well-known biologically compatible materials are suitable for fabrication of implantable 1devices. For example, small implants machined from titanium are easily polished and are well accepted by the human body. A wide range of plastic materials such as teflon are also biocompatible. For experimental purposes more easily machinable materials such as 405 stainless steel may be preferable to titanium and are also well tolerated. It has been found particularly advantageous to use titanium to encase the implantable device of the present invention. The titanium surface can be used as an auxiliary or third electrode for the detection system with the electronics within the case connected so as to maintain the auxiliary electrode at a constant potential relative to the reference electrode. The use of an auxiliary electrode allows the amperometric current to be carried by the case and, thus, be spread over a large area so that the current density is very low and will cause no biological effects.

The potential for current leakage problems exist with an enclosed titanium device unless the measuring electrode and the reference electrode are electrically isolated from the titanium case which acts as the auxiliary electrode. It has been found that the platinum in glass feed-through technology originally developed for high vacuum applications can be used for this purpose. Briefly, special types of glass that have coefficients of expansion nearly identical to platinum are available from Alberox Corp. A platinum wire may be passed through a bead of such a glass and the bead melted onto the platinum to make a water and gas tight junction. Such an insulator bead can then be potted into a hole drilled through the titanium case using, for example, laser welding.

Many researchers working on implantable glucose sensors may not appreciate the importance of sensor calibration. Both the enzyme mixture and the measuring electrode may change with time. Also, the microcirculation around the sensor may change so that the effective concentration of oxygen changes. Unless the enzyme mixture and measuring electrode response has the same slope at all possible oxygen concentration, this could significantly change the accuracy of the glucose measurements. Laboratory instruments are calibrated by being given analytes with known characteristics and then adjusting the instrument's output to match the known analyte. Unfortunately, it is not possible to easily expose an implanted sensor to a known concentration of glucose.

Considering that the implanted sensor is measuring a body compartment that is in equilibrium with the blood, blood glucose measurements can be used to effect calibration. If the patient takes a series of blood glucose measurements over time, these can be plotted against sensor output to develop a time constant for sensor response. Thereafter, blood glucose measurements can be used to automatically calibrate or adjust the implanted sensor.

Even though the device of the present invention is preferably implanted in a site away from direct blood circulation to avoid clotting problems, leukocytes will migrate out of the circulatory system to congregate around any "foreign" body. This leukocyte accumulation may damage the membrane or compromise the accuracy of the glucose readings. However, this problem can be largely avoided by incorporating an effective amount of an anti-inflammatory, anti-leukocyte compound into the enzyme mixture. One example is the addition of hydrocortisone, or similar cortical steroids such as cortisone and prednisolone, at about 0.1 to 1.0% by weight. These steroids can be dispersed in the aqueous phase of the enzyme mixture where they gradually dissolve and very slowly diffuse out through the outer membrane 12 keep the surrounding area free from attack by leukocytes.

Another serious impediment to long term sensor implants is that of microbial contamination by bacteria and fungi, etc. While microbes may directly destroy the glucose metabolizing enzyme, it is also likely for them to disrupt the glucose measurement by producing catalase or peroxidases which consumes the hydrogen peroxide before it can react with the electrode surface. The incorporation of antifungals or wide spectrum antibiotics into the enzyme mixture will largely prevent microbial interference. For example, gentamicin and/or penicillin, at about 0.1 to 0.8% percent by weight, and/or other broad spectrum antibiotics can be incorporated into the enzyme mixture to prevent bacterial interference.

The outer membrane 12 is generally believed to protect the glucose oxidase from various proteases. However, in the experiments leading to the present invention, it was discovered that stabilized glucose oxidase is not readily attacked by the common proteolytic enzyme trypsin. Therefore, trypsin may be incorporated in the outer membrane as an antiproteolytic enzyme to help destroy other proteolytic enzymes that might be produced by microorganisms, etc.

Stability of the enzyme mixture of the present invention can also be improved by the addition of antioxidants and/or free radical trapping agents. Vitamin E, which is also an oxygen solvent, can be incorporated into the enzyme mixture as can any of a number of "preservatives" such as various parabens, BHT (butylated hydroxy toluene) and its analogs, and/or superoxide dismutase.

In another embodiment of the invention a third membrane is situated between the enzyme-containing membrane and the electrode, i.e., so as to sandwich the enzyme containing membrane between the outer membrane and this third membrane. The function of the third membrane is to exclude compounds such as ascorbic acid and acetaminophen from interfering with the analysis. A cellulose acetate membrane can be used for this third membrane. See U.S. Pat. Nos. 3,979,274 and 4,073,713 to Newman.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

EXAMPLE 1

Preparation of Enyzme-Containing Membrane

Commercially available polytetrafluoroethylene and polydimethylsiloxane semi-interpenetrating polymer network membranes, also known as White Silon #320 (Bio Med Sciences, Inc.), were removed from their release liner, as membrane strips 2" by 3" and were rinsed with deionized water and ethanol. These membranes were stored in a bottle of sterilizing 70% Ethanol/deionized water, until they were used for enzyme studies.

The membranes were removed from their storage bottle and placed on a 4" by 4" glass plate. The strips of membrane were stretched out on a glass plate and blotted dry. Then approximately, 10 to 20 drops of a nonionic surfactant, Dimethylsiloxane-ethylene oxide copolymer, 20 cs., United Chemical Technologies, Inc.), were deposited on the membrane strips and the drops of surfactant were rubbed into the membrane structure with a smooth and blunt spatula. The membrane appearance turned translucent, which differed from it's original white opalescence. The strips of membrane were placed in a container and a 5% aqueous solution of the nonionic surfactant was poured into the container and the membranes were soaked for a period of at least 24 hours. The membranes are removed from the soaking solution and rinsed with deionized water until the membrane did not feel slippery. The membranes were again placed on a glass plate and blotted dry and then allowed to dry in the ambient laboratory environment.

The enzyme gelling solution for infiltration into the membranes was formulated with Glucose Oxidase, Type VII from Aspergillus Niger, EC 1.1.3.4 (Sigma Chemical Co.) and Bovine Serum Albumin, Fraction V Powder (Sigma Chemical Co.). About 0.1000 grams of Glucose Oxidase and 0.400 grams of Bovine Serum Albumin are mixed together in a 0.20 M Sodium Acetate (pH=5.00) (Sigma Chemical Co.) buffer, until they both dissolve in the acetate buffer (volume=7.5 ml). In a separate vial, a solution of 1.0 ml 25% Glutaraldehyde, Grade 1 (Sigma Chemical Co.) is mixed with 9.0 ml of acetate buffer (pH=5.00), which results in a 2.5% Glutaraldehyde/acetate buffer. A 2.5 ml aliquot of this 2.5% Glutaraldehyde/acetate buffer is removed and set aside for use later in crosslinking the enzyme gel in the pores of the modified White Silon #320 membrane. About 2.5 ml of the Glucose Oxidase/Bovine Serum Albumin solution is placed on the modified White Silon #320 membrane (one of the 2" by 3" strips of membrane on a glass plate) via a pipette. These drops wicked into the membrane and the solution was uniformly dispersed in the membrane by gently rubbing the membrane with a smooth blunt spatula. A visual judgement is made of the membrane after the Glucose Oxidase/Bovine Serum Albumin (GOD/BSA) is allowed to dry for about 30 minutes. If the solution of GOD/BSA has penetrated the pores of the membrane and evenly deposited within the pores the membrane will look a yellow translucent color. If there are gaps or incomplete deposition there will be spots of the membrane, which will not be colored yellow. After this visual inspection, about 0.8 ml of the 2.5% Glutaraldehyde/acetate buffer was added to the membrane as droplets and this solution was spread over the entire membrane area, in order to ensure even distribution of the cross-linking and immobilizing agent, Glutaraldehyde. The glass plate holding the GOD/BSA embedded White Silon #320 membrane was placed in a plastic zip lock bag (Glad), with a small amount of the 2.5% Glutaraldehyde solution in an open vial and left enclosed in this plastic bag for a period of 16 hours. The fully crosslinked and immobilized enzyme gel membrane was removed from this plastic bag and placed in another bag, which contained Gomori Buffer soaked cotton gauzes and the top of the bag was zipped shut. The buffer soaked gauzes maintained a humid environment for the enzyme gel membrane in the closed plastic bag, and the closed bag was marked with the appropriate date and laboratory notes and placed in a refrigerator for storage.

The membrane prepared as described above was very elastic and flexible, so long as it was wet. If the membrane was allowed to dry out it would become very brittle. However, with the addition of a water(buffer) the membrane became elastic once again. This drying out and rehydration cycle seems to be totally reversible, in that no loss of enzyme activity is noted. Also, there is no observable degradation of the mechanical properties for this enzyme embedded membrane. The thickness of membranes produced by the above procedure was in the range of from about 50 microns to 65 microns.

EXAMPLE 2

Preparation of Glucose Sensor

A glucose sensor in accordance with the present invention was prepared by punching a small disc (a #16 needle, about 0.1 mm) of the enzyme-containing membrane, prepared in Example 1 above. This disc is placed in a small vial with a milliliter of Gomori buffer. An electrode collar is solvent glued (methylene chloride) to an outer membrane made of polycarbonate. This assembly was set aside to dry, with the outer membrane lying on the bottom. After about 30 minutes, a small drop of Gomori buffer was placed in the "well" of the electrode collar. The small disc of enzyme-containing membrane was placed in the well and allowed to settle to the bottom of the well. This operation takes patience, in that, the disc of enzyme-containing membrane may need to be pushed under the meniscus of the drop of buffer in the well of the electrode collar. A platinum/ceramic electrode was glued into a titanium electrode port. This assembly was placed at the top of the well and the Platinum/Ceramic electrode is press fitted into the electrode collar.

The platinum/ceramic electrode is pushed into the electrode collar until it is seated flush with the top of the titanium electrode port. The enzyme-containing membrane disc was then clearly visible under the outer membrane, as a yellow disc.

What is claimed is:

1. An enzyme-containing membrane comprising a semi-interpenetrating polymer network of fibrillated polytetrafluoroethylene and a silicon compound wherein the network is infiltrated with an enzyme.

2. The membrane of claim 1 wherein the silicon compound is a cross-linked polyorganosiloxane.

3. The membrane of claim 2 wherein the polyorganosiloxane is polydimethylsiloxane.

4. The membrane of claim 1 wherein the enzyme oxidizes glucose and generates hydrogen peroxide.

5. The membrane of claim 4 wherein the enzyme is an oxidase.

6. The member of claim 1 wherein the enzyme is immobilized within said network.

7. The membrane of claim 6 wherein the enzyme is immobilized as an enzyme gel.

8. The membrane of claim 7 wherein the oxidase is glucose oxidase.

9. The membrane of claim 1 wherein the membrane has a porosity of from about 25% to about 55%.

10. The membrane of claim 9 wherein the membrane contains about 15 to 40% by volume of the silicon compound.

11. A membrane system comprising:
    an outer membrane; and
    an inner membrane, wherein the inner membrane is an enzyme-containing membrane having a semi-interpenetrating polymer network of fibrillated polytetrafluoroethylene and a silicon compound, wherein the network is infiltrated with an enzyme.

12. The membrane system of claim 9 wherein the outer membrane comprises polycarbonate.

13. The membrane system of claim 10 wherein the inner membrane contains about 15 to 40% by volume of said silicon compound.

14. The membrane system of claim 13 wherein the silicon compound of the enzyme-containing membrane is a cross-linked polyorganosiloxane.

15. The membrane system of claim 14 wherein the polyorganosiloxane is polydimethylsiloxane.

16. The membrane system of claim 9 wherein the enzyme of the enzyme-containing membrane is one or a combination of enzymes which oxidizes glucose and generates hydrogen peroxide.

17. The membrane system of claim 16 wherein the enzyme is immobilized in said inner membrane.

18. The membrane system of claim 17 wherein the enzyme is immobilized as an enzyme gel.

19. The membrane system of claim 16 wherein the enzyme is an oxidase.

20. The membrane system of claim 19 wherein the oxidase is glucose oxidase.

21. The membrane system of claim 20 wherein the enzyme-containing membrane has a porosity of from about 25% to about 55%.

22. A glucose sensor comprising:
    a membrane system having an outer membrane and an inner membrane, wherein the inner membrane is an enzyme-containing membrane which includes a semi-interpenetrating polymer network of fibrillated polytetrafluoroethylene and a silicon compound, wherein the network is infiltrated by an enzyme, and wherein the outer membrane restricts the flow of glucose into the inner membrane;
    an electrode which oxidizes hydrogen peroxide; and
    wherein the inner membrane is disposed between the outer membrane and the electrode.

23. The glucose sensor of claim 22 wherein the outer membrane of the membrane system comprises polycarbonate.

24. The glucose sensor of claim 22 wherein the silicon compound of the enzyme-containing membrane is a cross-linked polyorganosiloxane.

25. The glucose sensor of claim 24 wherein the polyorganosiloxane is polydimethylsiloxane.

26. The glucose sensor of claim 22 wherein the enzyme of the enzyme-containing membrane is one or a combination of enzymes which oxidizes glucose and generates hydrogen peroxide.

27. The glucose sensor of claim 26 wherein the enzyme is an oxidase.

28. The glucose of claim 27 wherein the oxidase is glucose oxidase.

29. The glucose sensor of claim 22 wherein the enzyme is immobilized in the enzyme-containing membrane.

30. The glucose sensor of claim 22 wherein the enzyme is immobilized as an enzyme gel.

31. The glucose sensor of claim 22 wherein the enzyme-containing membrane has a porosity of from about 25% to about 55%.

* * * * *

UNITED STATES PATENT AND TRADEMARK OFFICE
CERTIFICATE OF CORRECTION

PATENT NO.    :   5,964,993
DATED         :   October 12, 1999
INVENTOR(S)   :   Elmo A. Blubaugh, Jr. et al.

It is certified that error appears in the above-identified patent and that said Letters Patent is hereby corrected as shown below:

Claim 12, col. 13, line 37, "9" should be --11--.
Claim 13, col. 13, line 39, "10" should be --11--.
Claim 16, col. 13, line 47, "9" should be --11--.
Claim 21, col. 14, line 9, "20" should be --11--.
Claim 28, col. 14, line 40, after "glucose" insert --sensor--.

Signed and Sealed this

Eleventh Day of April, 2000

Q. TODD DICKINSON

Attest:

Attesting Officer

*Director of Patents and Trademarks*